(12) United States Patent
Hayakawa

(10) Patent No.: US 11,179,121 B2
(45) Date of Patent: Nov. 23, 2021

(54) X-RAY IMAGING DEVICE

(71) Applicant: Shimadzu Corporation, Kyoto (JP)

(72) Inventor: Toru Hayakawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 1 day.

(21) Appl. No.: 16/954,927

(22) PCT Filed: Nov. 5, 2018

(86) PCT No.: PCT/JP2018/041016
§ 371 (c)(1),
(2) Date: Jun. 17, 2020

(87) PCT Pub. No.: WO2019/150682
PCT Pub. Date: Aug. 8, 2019

(65) Prior Publication Data
US 2020/0390409 A1    Dec. 17, 2020

(30) Foreign Application Priority Data
Feb. 2, 2018    (JP) .............................. JP2018-017305

(51) Int. Cl.
*A61B 6/00*    (2006.01)
(52) U.S. Cl.
CPC .......... *A61B 6/4452* (2013.01); *A61B 6/4405* (2013.01)

(58) Field of Classification Search
CPC .............................. A61B 6/447; A61B 6/4405
See application file for complete search history.

(56) References Cited

FOREIGN PATENT DOCUMENTS

| JP | 2004-33415 A | 2/2004 |
| JP | 2011-68419 A | 4/2011 |

OTHER PUBLICATIONS

Written Opinion for PCT application PCT/JP2018/041016 dated Jan. 29, 2019, submitted with a machine translation.

*Primary Examiner* — Dani Fox
(74) *Attorney, Agent, or Firm* — Muir Patent Law, PLLC

(57) ABSTRACT

When a wire rope (55) is broken, the wire rope (55) will sag from the state in which the wire rope is tensioned with a predetermined tension. At this time, a pin (71) is pressed toward a movable support (42) by a biasing force of a spring (73), and the tip of the pin (71) is brought into contact with the surface of the movable support (42). When the support arm (43) is ascended or descended with respect to the movable support (42) and the pin (71) is arranged at a position facing the hole (65) formed in the movable support (42), the tip of the pin (71) is entered into the hole (65), so that the pin (71) and the hole (65) are engaged with each other. Thereby, the support arm (43) is fixed with respect to the movable support (42).

6 Claims, 9 Drawing Sheets

X-RAY IMAGING DEVICE

TECHNICAL FIELD

The present invention relates to an X-ray imaging apparatus in which an X-ray tube or an X-ray detector is supported by a wire rope in a suspended manner.

BACKGROUND OF THE INVENTION

As such an X-ray imaging apparatus, a mobile X-ray imaging apparatus for performing X-ray imaging by traveling between hospital rooms has been used. This mobile X-ray imaging apparatus is provided with a main body having a front wheel and a rear wheel, a support provided vertically upward on the main body, a support arm ascendable and descendable along the support in a state in which an X-ray irradiation unit composed of an X-ray tube and a collimator is supported or pivotable about the support, an X-ray detector for detecting X-rays irradiated from the X-ray irradiation unit and passed through a subject, and a battery arranged inside the main body.

In such a mobile X-ray imaging apparatus, the X-ray irradiation unit composed of the X-ray tube and the collimator needs to be ascended and descended together with the support arm depending on the state of imaging. The ascending and descending mechanism of this support arm is provided with a pulley provided at the upper portion of the support and a wire rope wound around the pulley with one end of the wire rope fixed to the support arm and the other end thereof fixed to the support, and is configured to support the support arm in a suspended manner by the wire rope.

In such a mobile X-ray imaging apparatus, there is a risk that the wire rope is broken, resulting in dropping of the support arm together with the X-ray tube and the collimator. For this reason, conventionally, an X-ray imaging apparatus has been proposed in which a mechanical stopper mechanism for stopping a support arm at a position where the wire rope is broken is equipped as a safety mechanism in case of breakage of the wire rope (see Patent Documents 1 and 2).

PRIOR ART DOCUMENT

Patent Document

Patent Document 1: Japanese Unexamined Patent Application Publication No. 2004-33415
Patent Document 2: Japanese Unexamined Patent Application Publication No. 2011-68419

SUMMARY OF THE INVENTION

Problems to be Solved by the Invention

In the case of adopting a mechanism for preventing the dropping of a support arm or the like supporting an X-ray tube and a collimator by a mechanical stopper mechanism, depending on the stopping position of the support arm, the subsequent restoration operation is hindered. For example, in cases where the support arm is stopped at a high position, not only the center of gravity becomes high, resulting in an unstable state at the time of traveling, but also the apparatus cannot travel through a region limited in height such as a region having a door, etc. Further, in cases where the support arm is turned sideways and stopped at a low position from which turning is impossible, not only the region occupied by the apparatus in the width-direction becomes large, which prevents the traveling of the apparatus through a region limited in the width such as a region having a door, etc., but also, depending on the posture of the support arm, the support arm is arranged in front of the operation region of the apparatus, so that the operation becomes impossible.

In order to solve such problems, it is conceivable to adopt a configuration in which a pair of wire ropes is used so that even if one of the wire ropes is broken, the support arm, etc., is supported by the other wire rope to prevent the dropping of the support arm, etc. In cases where such a configuration is adopted, the operator is required to check the state of the pair of wire ropes in the daily inspection and stop the use of the apparatus if the wire rope is damaged or broken, and the apparatus is repaired.

However, even in cases where such a configuration is adopted, if an adequate inspection is not performed and the apparatus is continuously used in a state in which one of the wire ropes is broken, there is a possibility that the other wire rope is also broken, causing an accident that the support arm drops.

For this reason, it is conceivable to adopt a configuration in which a breakage detection mechanism having a sensor such as a microswitch is attached to each of a pair of wire ropes and the operation of the apparatus is electrically stopped when either one of the pair of wire ropes is broken. However, in the case of adopting such a configuration, not only a configuration becomes complicated due to the existence of the sensor and its wirings, causing a complicated configuration and an increased cost, but also the control system becomes complicated.

Such a problem occurs not only in cases where an X-ray tube and/or a collimator is ascended or descended in a mobile X-ray imaging apparatus but also in cases where an X-ray tube and/or a collimator is ascended or descended in an X-ray imaging apparatus for ordinary imaging or in cases where an X-ray detector, such as, e.g., a flat panel detector, is ascended or descended in a standing posture imaging apparatus or the like.

The present invention has been made to solve the above-described problems, and an object of the present invention is to provide an X-ray imaging apparatus capable of stopping a support member at a suitable position at the time of a breakage of a wire rope in cases where an X-ray tube and/or an X-ray detector is supported by a pair of wire ropes.

Means for Solving the Problem

The invention as recited in claim 1 relates to an X-ray imaging apparatus comprising:
a support member configured to support an X-ray tube or an X-ray detector;
a pair of wire ropes configured to support the support member in a suspended manner;
and
a pair of engagement mechanisms each including an engaging member movable between an engagement position engageable with a hole formed in a fixed side member and a separation position spaced apart from the hole and a biasing means biasing the engaging member toward the engagement position, the pair of engagement mechanisms being provided on the support member so as to correspond to the pair of wire ropes,
wherein the engaging member of the engagement mechanism is arranged at the separation position against a biasing force of the biasing means in a state in which the engaging member is in contact with the wire rope.

According to the invention as recited in claim 2, in the invention as recited in claim 1, the wire rope is wound around a pulley with one end of the wire rope fixed to the support member and the other end thereof fixed to the fixed side member.

According to the invention as recited in claim 3, in the invention as recited in claim 1 or 2, the engaging member is a pin provided with a recess capable of accommodating the wire rope and configured such that a bottom surface of the recess is capable of coming into contact with the wire rope.

According to the invention as recited in claim 4, an X-ray imaging apparatus includes:

a support;

a support arm arranged in an ascendable and descendable manner with respect to the support and configured to support an X-ray tube and;

a pair of pulleys provided on an upper portion of the support;

a pair of wire ropes each wound around the corresponding pulley with one end of the wire rope fixed to the support arm and the other end thereof fixed to the support; and a pair of engagement mechanisms each including an engaging member movable between an engagement position engageable with a hole formed in the support and a separation position spaced apart from the hole and a biasing means biasing the engaging member toward the engagement position, the pair of engagement mechanisms being provided on the support arm so as to correspond to the pair of wire ropes, wherein the engaging member of the engagement mechanism is arranged at the separation position against a biasing force of the biasing means in a state in which the engaging member is in contact with the wire rope.

According to the invention as recited in claim 5, in the invention as recited in claim 4, the X-ray imaging apparatus further includes:

a second support configured to support the support in an ascendable and descendable manner;

a pair of second pulleys provided on an upper portion of the second support;

a pair of second wire ropes each wound around the corresponding second pulley with one end of the second wire rope fixed to the support and the other end thereof fixed to the second support;

a pair of second engagement mechanisms each including a second engaging member movable between an engagement position engageable with a hole formed in the second support and a separation position spaced apart from the hole and a second biasing means biasing the second engaging member toward the engagement position, the pair of engagement mechanisms being provided on the support so as to correspond to the pair of second wire ropes, wherein the second engaging member of the second engagement mechanism is arranged at the separation position against a biasing force of the second biasing means in a state in which the second engaging member is in contact with the second wire rope.

Effects of the Invention

According to the invention described in claim 1, by the action of the engagement mechanism, it is possible to engage the engaging member with the hole formed in the fixed side member at the time of the breakage of the wire rope to stop the ascending and descending of the support member. Therefore, by setting the position of the hole to be formed in the fixed side member to an appropriate position, even in cases where the wire rope is broken, it is possible to safely stop the support member at a suitable position.

According to the invention as recited in claim 2, in the ascending and descending mechanism using the pulley, it is possible to safely stop the support member at a suitable position.

According to the invention as recited in claim 3, in a state in which the wire ropes are not broken, by accommodating the wire ropes in the recesses, the engaging members can be assuredly arranged at the separation positions.

According to the invention as recited in claim 4, by the action of the engagement mechanism, it is possible to engage the engaging member with the hole formed in the support at the time of the breakage of the wire rope to stop the ascending and descending of the support arm. Therefore, by setting the position of the hole to be formed in the support to an appropriate position, even in the case where the wire rope is broken, it is possible to safely stop the support arm at an appropriate position.

According to the invention as recited in claim 5, even in cases where the support arm is ascended and descended in two stages using the support and the second support, even in the case where the second wire rope is broken, the support can be safely stopped at an appropriate position.

EMBODIMENTS FOR CARRYING OUT THE INVENTION

Figure 1:
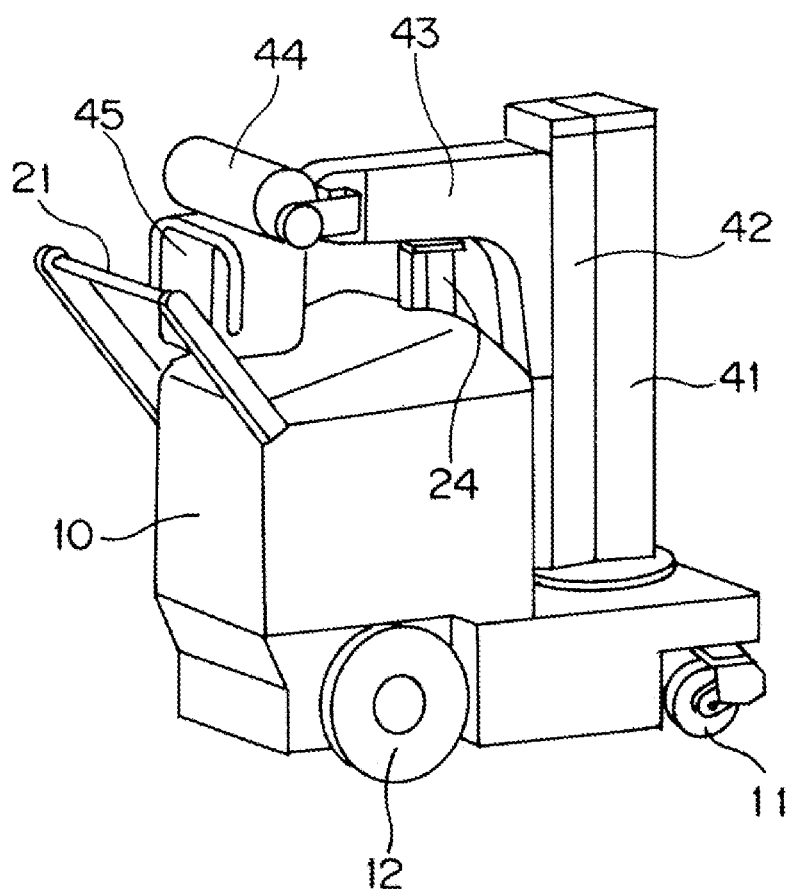
FIG. 1 is a perspective view of an X-ray imaging apparatus according to a first embodiment of the present invention.
Figure 2:
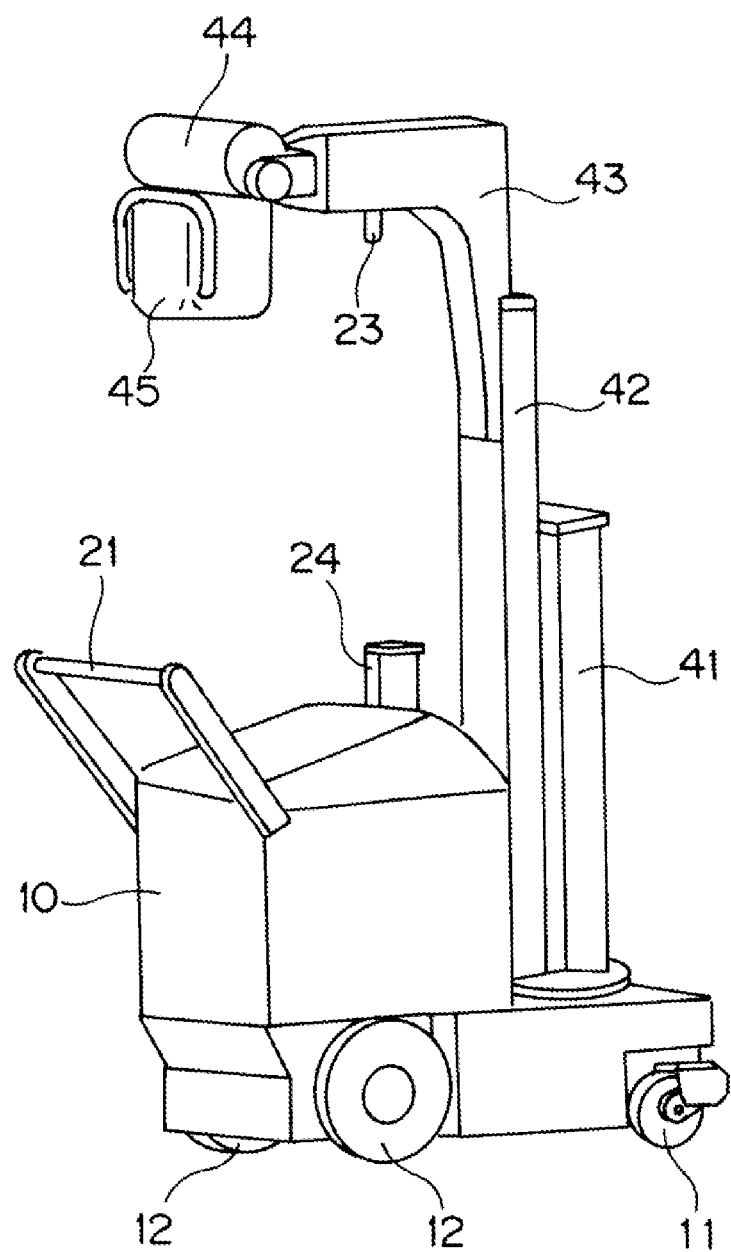
FIG. 2 is a perspective view of an X-ray imaging apparatus according to a first embodiment of the present invention.
Figure 3:
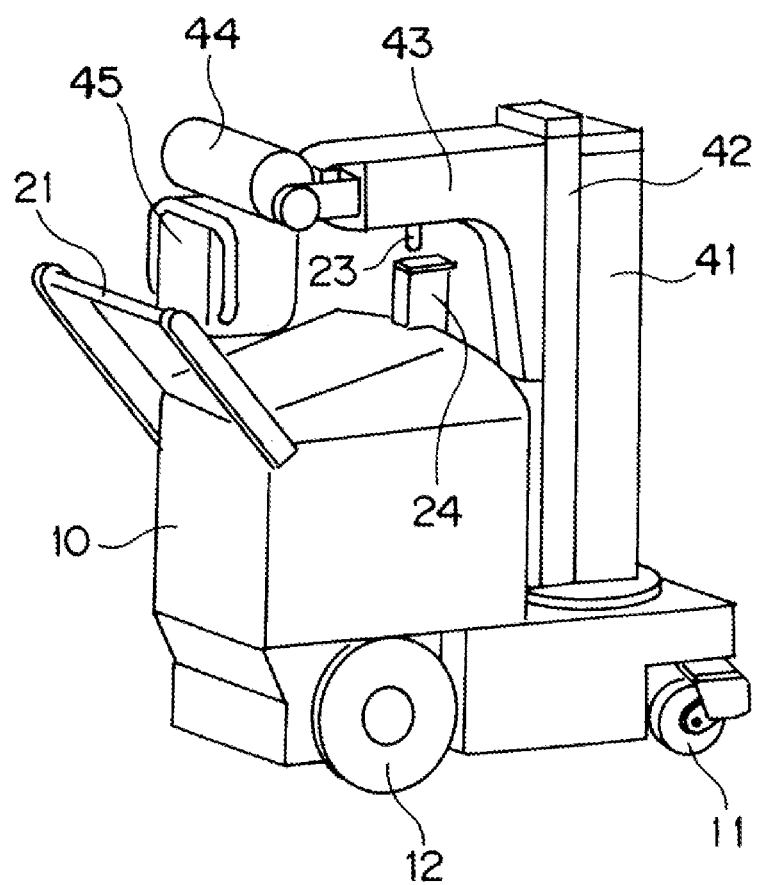
FIG. 3 is a perspective view of an X-ray imaging apparatus according to a first embodiment of the present invention.

Hereinafter, an embodiment of the present invention will be described with reference to the attached drawings. FIG. 1 to FIG. 3 are perspective views of an X-ray imaging apparatus according to a first embodiment of the present invention. Note that FIG. 1 shows a state in which the support arm 43 is arranged at the fixing position, which is a position to be arranged at the time of traveling the X-ray imaging apparatus. FIG. 2 shows a state in which the support arm 43 is arranged at the ascended position ascended from the fixing position. FIG. 3 shows a state in which the support arm 43 is arranged at the ascending and descending stop position, which is a position to be arranged at the time of the breakage of the wire rope 53 or 55, which will be described later.

This X-ray imaging apparatus is referred to also as an X-ray imaging apparatus for rounds, and is configured to travel between a plurality of hospital rooms to perform an X-ray inspection in each hospital room. This X-ray imaging apparatus is provided with a carriage 10, a pair of right and left front wheels 11, which are wheels for changing directions, arranged on the front side of the traveling direction of the carriage 10, and a pair of right and left rear wheels 12, which are wheels for driving, arranged on the rear side of the traveling direction of the carriage 10. The rear wheels 12 are rotated by a drive of a motor mounted on the carriage 10.

On the front side of the traveling direction of the carriage 10, a fixed support 41 constituting a second support according to this invention is provided in the vertically extended manner. To this fixed support 41, a movable support 42 constituting the support according to this invention and a support arm 43 are provided in an ascendable and descendable manner. The support arm 43 has a substantially L-shape in a side view, and an X-ray irradiation unit composed of an X-ray tube 44 and a collimator 45 is provided at the distal end of the L-shaped support arm. The X-ray tube 44 and the collimator 45 are ascended and descended in accordance with the ascending and descending operation of the movable support 42 and the support arm 43. The fixed support 41 is rotatably supported about a vertical axis, and the X-ray tube 44 and the collimator 45 are pivotable together with the support arm 43 in accordance with the rotation of the fixed support 41.

A pin 23 is provided on the lower surface of the support arm 43. The carriage 10 is provided with a locking portion 24 called an arm catch. In the state in which the support arm 43 is positioned at the fixing position shown in FIG. 1, the lower surface of the support arm 43 is in contact with the locking portion 24. In this state, the pin 23 provided on the lower surface of the support arm 43 is accommodated in the hole (not shown) formed in the locking portion 24.

The carriage 10 is provided with an operation handle 21 for operating the traveling direction of the apparatus and a storage portion (not shown) for accommodating an X-ray detector (not shown), such as a flat panel detector, for detecting X-rays emitted from the X-ray tube 44 and passed through a subject.

Figure 4:
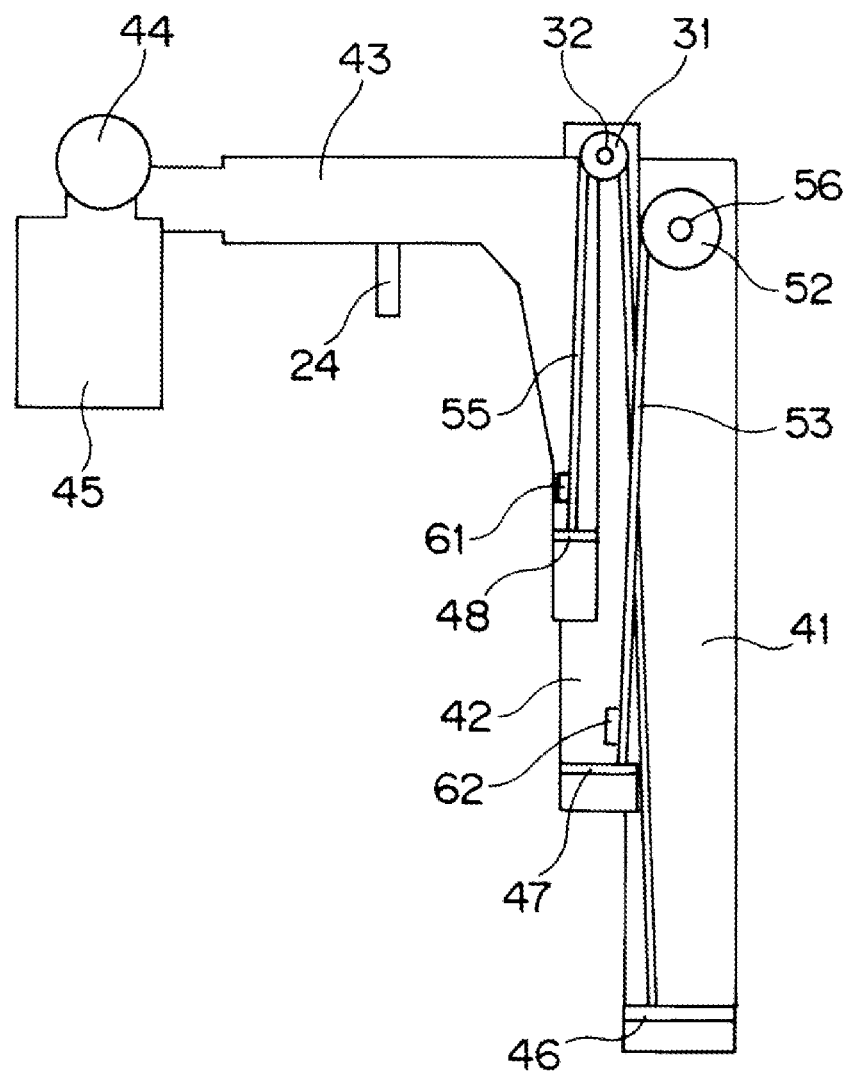
FIG. 4 is a schematic side view of a fixed support 41, a movable support 42, and a support arm 43.
Figure 5:
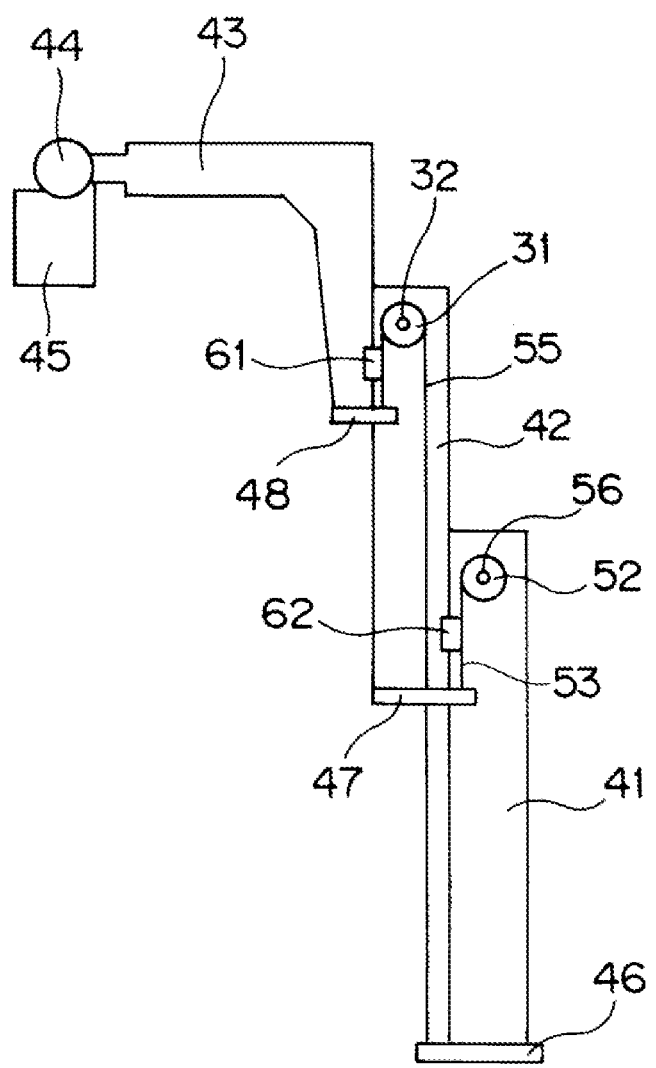
FIG. 5 is a schematic side view for explaining an ascending and descending operation of a movable support 42 and a support arm 43.

FIG. 4 is a schematic side view of the fixed support 41, the movable support 42, and the support arm 43. FIG. 5 is a schematic side view for explaining the ascending and descending operation of the movable support 42 and the support arm 43.

The movable support 42 is configured to be ascendable and descendable along the fixed support 41 by a guide member (not shown) provided on the fixed support 41. The support arm 43 is configured to be ascendable and descendable along the movable support 42 together with the X-ray tube 44 and the collimator 45 by a guide member (not shown) provided on the movable support 42.

At the upper portion of the fixed support 41, a winding pulley 52 connected to an ascending and descending auxiliary mechanism provided with a spring or the like is arranged so as to be rotatable about a shaft 56 fixed to the upper portion of the fixed support 41. A wire rope 53 is wound around the winding pulley 52 with one end of the wire rope fixed to the winding pulley and the other end thereof fixed to a base portion 47 provided at the lower end of the movable support 42. With this configuration, in accordance with the change in the winding quantity of the wire rope 53 wound around the winding pulley 52 caused by the rotation of the winding pulley 52, the movable support 42 is ascended and descended. Note that the winding pulley 52 constitutes the second pulley according to the present invention and the wire rope 53 constitutes the second wire rope according to the present invention.

On the other hand, at the upper portion of the movable support 42, a fixed pulley 31 as a pulley according to the present invention is provided so as to be rotatable about a support shaft 32 fixed to the upper portion of the movable support 42. A wire rope 55 for ascending and descending the support arm 43 is wound around the fixed pulley 31 with one end of the wire rope fixed to a base portion 46 provided at the lower end portion of the fixed support 41 and the other end thereof fixed to a base portion 48 provided at the lower end portion of the support arm 43. With this configuration, when the movable support 42 is ascended by the action of the wire rope 53 and the wire rope 55 is unwound toward the base portion 46, the support arm 43 is also ascended with respect to the movable support 42. On the other hand, when the movable support 42 is descended and the wire rope 55 is unwound toward the base portion 48, the support arm 43 also is descended with respect to the movable support 42.

Therefore, when the movable support 42 is ascended in accordance with the rotation of the winding pulley 52, as shown in FIG. 5, the support arm 43 is ascended twice as much as the ascending quantity of the movable support 42 together with X-ray irradiation unit composed of the X-ray tube 44 and the collimator 45. Further, when the movable support 42 is descended in accordance with the rotation of the winding pulley 52, as shown in FIG. 4, the support arm 43 is descended twice as much as the descending quantity of the movable support 42 together with the X-ray irradiation unit composed of the X-ray tube 44 and the collimator 45.

Note that the above-described wire ropes 53 and 55 are each composed of a pair of wire ropes arranged in parallel with each other. Further note that the above-described winding pulley 52 and fixed pulley 31 for winding the wire ropes 53 and 55 are each composed of a pair of pulleys arranged coaxially. With this configuration, even in cases where one of the wire ropes 53 and 55 is broken by fatigue or the like, the movable support 42 and the support arm 43 can be prevented from the dropping by the other wire rope 53 and 55. A stopper mechanism 61 for safely stopping the support arm 43 at a suitable position when one of the pair of wire ropes 55 is broken is provide, and a stopper mechanism 62 for safely stopping the movable support 42 at a suitable position when one of the pair of wire ropes 53 is broken is provided.

When the movable support 42 and the support arm 43 are ascended, the support arm 43 is arranged at the ascended position as shown in FIG. 2. In this situation, when the fixed support 41 is rotated about an axis extending in the vertical direction with respect to the carriage 10, the X-ray irradiation unit composed of the X-ray tube 44 and the collimator 45 rotates together with the support arm 43. This allows the X-ray irradiation unit composed of the X-ray tube 44 and the collimator 45 to be placed in a position suitable for X-ray imaging.

On the other hand, in a state in which the movable support 42 and the support arm 43 are descended and the support arm 43 is arranged at the fixing position as shown in FIG. 1, the lower surface of the support arm 43 comes into contact with the locking portion 24 and the pin 23 provided on the lower surface of the support arm 43 is accommodated in the hole formed in the locking portion 24. In this situation, it becomes possible to travel the X-ray imaging apparatus between hospital rooms and the like.

Figure 6:
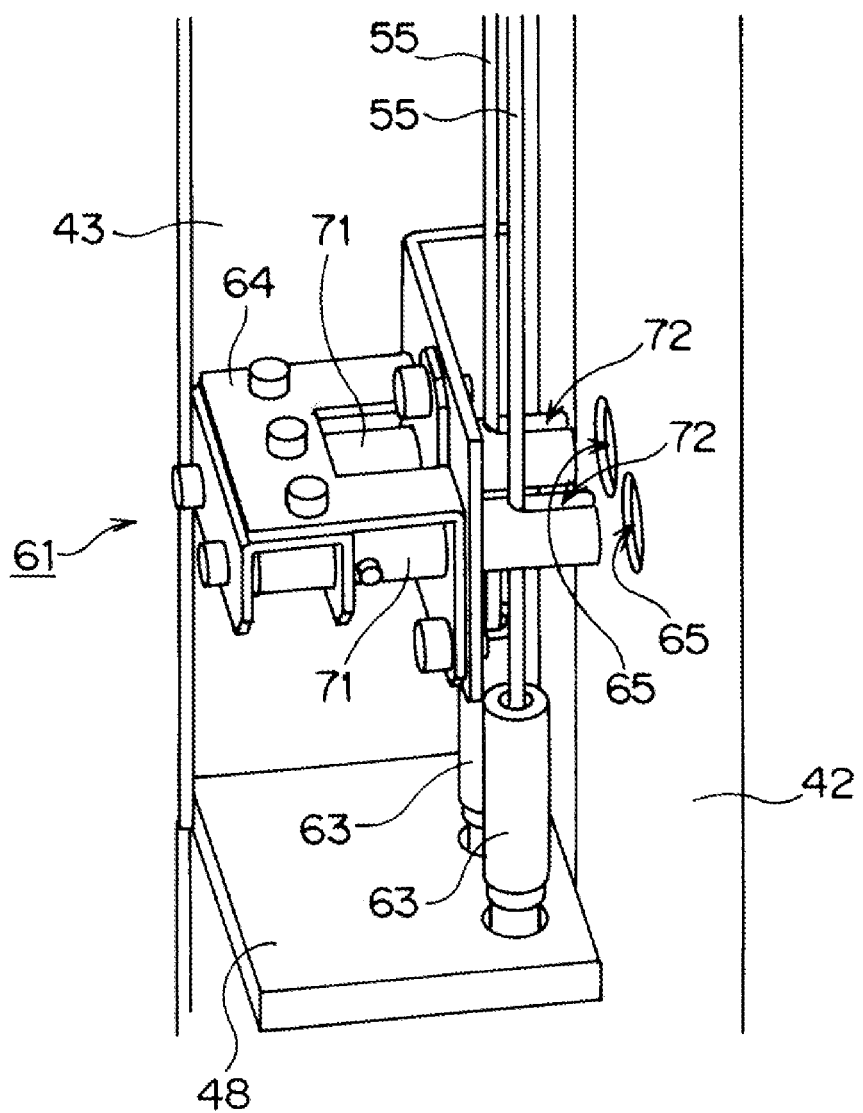
FIG. 6 is an enlarged perspective view of the vicinity of a stopper mechanism 61.
Figure 7:
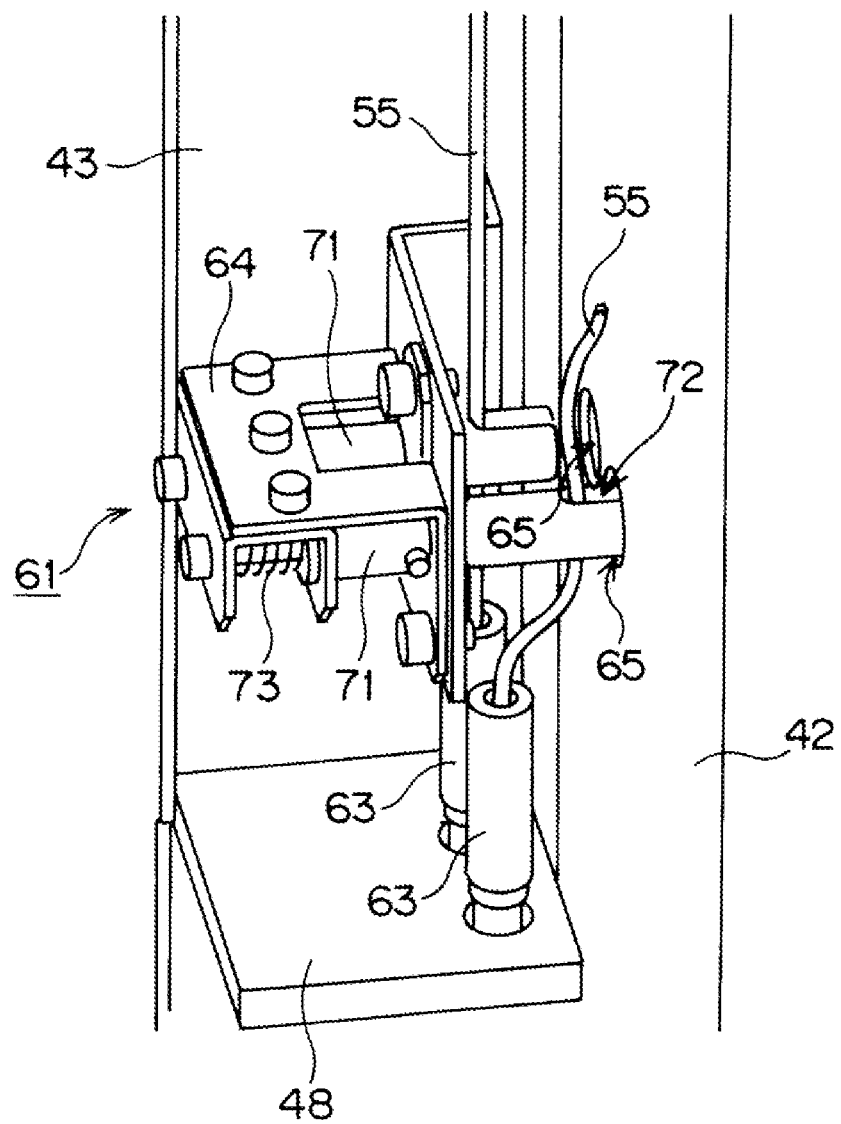
FIG. 7 is an enlarged perspective view of the vicinity of a stopper mechanism 61.

Next, the configuration of the stopper mechanism 61 and 62, which is a characteristic part of the present invention, will be described. FIG. 6 and FIG. 7 are enlarged perspective views of the vicinity of the stopper mechanism 61. Here, FIG. 6 shows the state in which a pair of pins 71 are each arranged at the separation position, and FIG. 7 shows the state in which one pin 71 out of the pair of pins 71 is arranged at the engagement position. Note that in the following description, the configuration of the stopper mechanism 61 out of the stopper mechanisms 61 and 62 shown in FIG. 4 and FIG. 5 will be described, but the stopper mechanism 62 has the same configuration.

This stopper mechanism 61 is provided with a support bracket 64 fixed to the support arm 43 as a support member, a pair of pins 71 arranged so as to be reciprocally movable with respect to the support bracket 64 at positions opposed to the pair of wire ropes 55, and a pair of springs 73 for biasing the respective pins 71 (see FIG. 7). These pins 71 and springs 73 constitute the engagement mechanisms according to the present invention which are arranged so as to correspond with the pair of wire ropes 55. The pin 71 functions as an engaging member according to the present invention, and is formed at the tip end thereof with a recess 72 capable of accommodating the wire rope 55. The wire rope 55 is fixed to the base portion 48 via the mounting bracket 63.

The pin 71 is movable between an engagement position in which the pin is entered in the hole 65 formed in the surface of the movable support 42 which functions as a fixed side member according to the present invention and is engaged with the hole 65 and a separation position spaced apart from the hole 65. Then, as shown in FIG. 6, each pin 71 is arranged at the separation position against the biasing force of the spring 73 in a state in which the bottom surface in the recess 72 is in contact with the wire rope 55 accommodated in the recess 72.

In this state, when the wire rope 55 is broken by the fatigue or the like, the wire rope 55 will sag from the tensioned state with a predetermined tension. In this state, the pin 71 is pushed toward the movable support 42 by the biasing force of the spring 73, and the tip of pin 71 is brought into contact with the surface of the movable support 42. When the support arm 43 is ascended or descended with respect to the movable support 42, the pin 71 is slidably moved on the surface of the movable support 42 and is arranged at the position facing the hole 65 formed in the surface of the movable support 42, as shown in FIG. 7, the tip end of the pin 71 enters the hole 65, so that the pin 71 and the hole 65 are engaged with each other. With this, the support arm 43 is fixed to the movable support 42. Therefore, by setting the position of the hole 65 to be formed in the surface of the movable support 42 to an appropriate position, it is possible to stop the support arm 43 at a height position suitable for the subsequent operation.

Note that in the stopper mechanism 62, by the same configuration as that shown in FIG. 6 and FIG. 7, it is possible to engage the pin in the stopper mechanism 62 with the hole formed in the surface of the fixed support 41 to fix the movable support 42 to the fixed support 41. At this time, the support arm 43 and the movable support 42 are ascended and descended in synchronization with each other, and when one is fixed, the other is fixed. For this reason, at the height position at which the pin 71 in the stopper mechanism 61 is engaged with the hole 65 formed in the surface of the movable support 42, by forming a hole in the surface of the fixed support 41 at a position at which the pin 71 in the stopper mechanism 62 can be engaged with the hole formed in the surface of the fixed support 41, it becomes possible to stop the support arm 43 and the movable support 42 at the same height position even in cases where either one of the wire rope 53 and the wire rope 55 is broken.

FIG. 3 shows a height position at which the support arm 43 and the movable support 42 are stopped when one of the pair of wire ropes 53 and 55 is broken when the above-described configuration is employed. In this state, the support arm 43 is arranged at a lower position in a range in which the pin 23 provided on the lower surface of the support arm 43 is not accommodated in the hole formed in the locking portion 24. As a result, it is possible not only to take a stable posture which is low in the center of gravity of the entire apparatus and but also to lower the height of the entire apparatus. Further, since the pin 23 provided on the lower surface of the support arm 43 is not engaged with the locking portion 24, the support arm 43 can be freely rotated to a position suitable for the subsequent operation.

Figure 8:
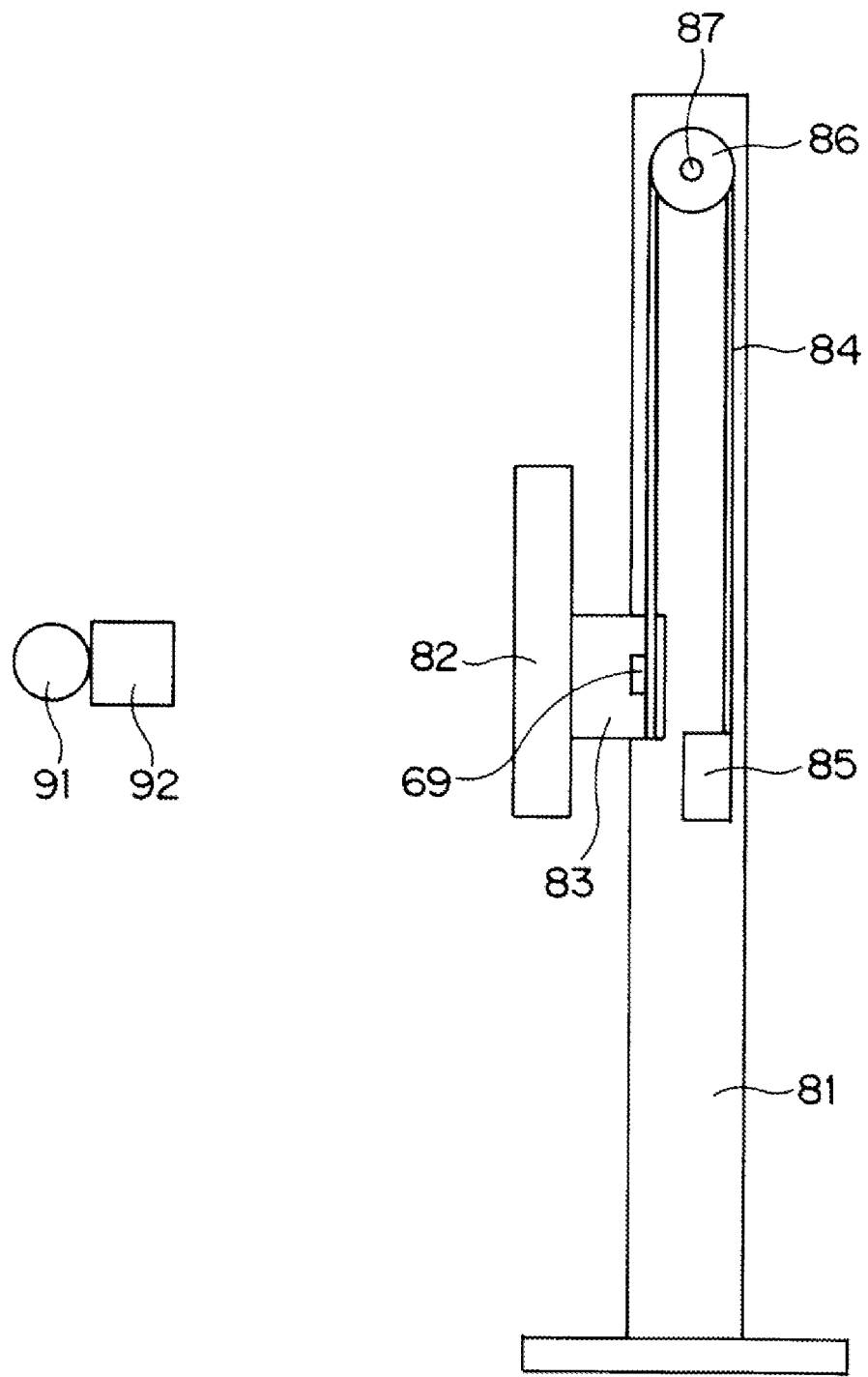
FIG. 8 is a schematic side view of an X-ray imaging apparatus according to a second embodiment of the present invention.
Figure 9:
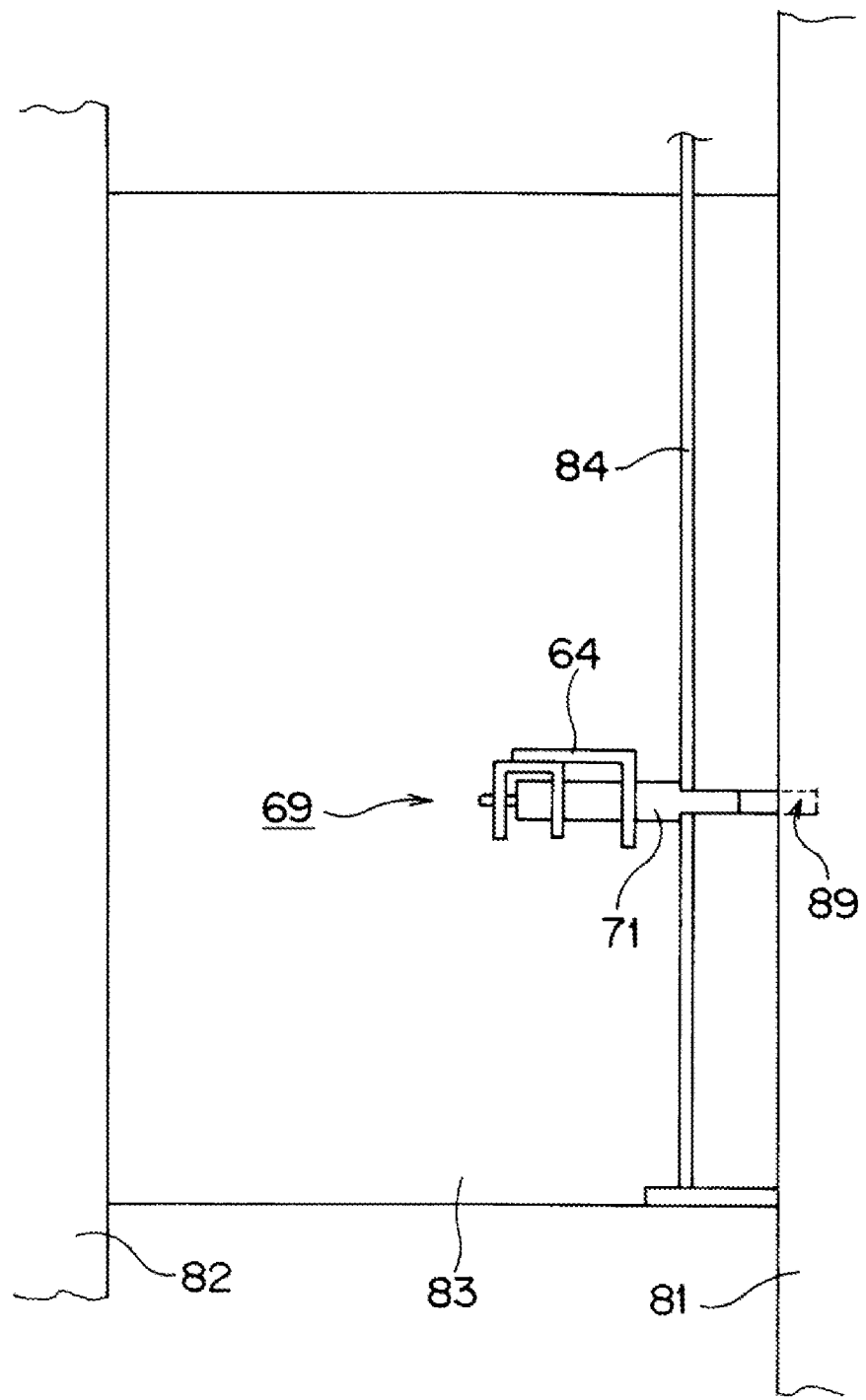
FIG. 9 is an enlarged view of a side portion of an X-ray imaging apparatus according to a second embodiment of the present invention.

Next, another embodiment of the present invention will be described. FIG. 8 is a schematic side view of an X-ray imaging apparatus according to a second embodiment of the present invention. FIG. 9 is an enlarged side partial view of the X-ray imaging apparatus according to the second embodiment of the present invention.

This X-ray imaging apparatus is referred to also as a standing posture imaging apparatus and is provided with an X-ray detector 82 such as a flat panel detector for detecting X-rays emitted from an X-ray irradiation unit composed of an X-ray tube 91 and a collimator 92 and passed through a subject. The X-ray detector 82 is supported by a support block 83 and can be ascendable and descendable with respect to the main body 81 by a guide mechanism (not shown) provided on the main body 81.

A fixed pulley 86 which rotates about a shaft 87 is arranged at the upper portion of the main body 81. Around this fixed pulley 86, a wire rope 84 having one end connected to the support block 83 and the other end connected to a counterweight 85 having a weight equivalent to the weight of the X-ray detector 82 and the support block 83 is wound. As a result, the X-ray detector 82 can be ascended and descended with a small force together with the support block 83 in accordance with the operation by the operator.

Note that the above-mentioned wire rope 84 is composed of a pair of wire ropes arranged in parallel with each other. Also note that the fixed pulley 86 for winding the wire rope 84 is composed of a pair of fixed pulleys coaxially arranged. Thus, even in cases where the wire rope 84 is broken by the fatigue or the like, it is possible to prevent the dropping of the X-ray detector 82 and the counterweight 85. A stopper mechanism 69 is provided for safely stopping the X-ray detector 82 at a suitable position in cases where one of the pair of wire ropes 84 is broken.

As shown in FIG. 9, the stopper mechanism 69 is provided with a support bracket 64 fixed to a support block 83 as a support member, a pair of pins 71 arranged so as to be reciprocally movable with respect to the support bracket 64 in a position opposed to the pair of wire ropes 84, and a pair of springs (not shown) for biasing the respective pins 71. Note that the pin 71 and the spring constitute the engagement mechanism according to the present invention which is arranged corresponding to the pair of wire ropes 84. Each pin 71 functions as the engaging member according to the present invention, and in the same manner as in the embodiment shown in FIG. 6 and FIG. 7, a recess capable of accommodating the wire rope 84 is formed at the distal end thereof.

The pin 71 is movable between an engagement position at which the pin enters into a hole 89 formed in the surface of the main body 81 which functions as a fixed side member according to the present invention and is engaged with the hole 89 and a separation position spaced apart from the hole 89. Each pin 71 is arranged at the separation position against the biasing force of the spring in a state in which the bottom surface of the recess is in contact with the wire rope 84 accommodated in the recess formed in the each pin 71.

In this state, in cases where the wire rope 84 is broken by the fatigue or the like, the wire rope 84 will sag from the tensioned state with a predetermined tension. At this time, the pin 71 is pressed toward the main body 81 by the biasing force of the spring, and the tip end of the pin 71 is brought into contact with the surface of the main body 81. Then, when X-ray detector 82 is ascended or descended relative to the main body 81 together with the support block 83 and the pin 71 slides on the surface of the main body 81 and is arranged at the position facing the hole 89 formed in the surface of the main body 81, the tip end of the pin 71 is entered in the hole 89, so that the pin 71 and the hole 89 are engaged with each other. Thereby, the X-ray detector 82 and the support block 83 are fixed relative to the main body 81. Therefore, by setting the position of the hole 89 to be formed in the surface of the main body 81 to an appropriate position, it is possible to stop the X-ray detector 82 at a height position suitable for the subsequent operation.

DESCRIPTION OF SYMBOLS

10: carriage
11: Front wheel
12: Rear wheel
31: Fixed pulley
41: Fixed support
42: Movable support
43: Support arm
44: X-ray tube
45: Collimator
52: Winding pulley
53: Wire rope
55: Wire rope
61: Stopper mechanism
62: Stopper mechanism
64: Support bracket
65: Hole
69: Stopper mechanism
71: Pin
72: Recess
73: Spring
81: Main body
82: X-ray detector
83: Support block
84: Wire rope
89: Hole

The invention claimed is:

1. An X-ray imaging apparatus comprising:
a support member configured to support an X-ray tube or an X-ray detector;
a pair of wire ropes configured to support the support member in a suspended manner; and
a pair of engagement mechanisms each including an engaging member movable between an engagement position engageable with a hole formed in a fixed side member and a separation position spaced apart from the hole and a biasing means biasing the engaging member toward the engagement position, the pair of engagement mechanisms being provided on the support member so as to correspond to the pair of wire ropes,
wherein the engaging member of the engagement mechanism is arranged at the separation position against a biasing force of the biasing means in a state in which the engaging member is in contact with the wire rope.

2. The X-ray imaging apparatus as recited in claim 1, wherein the wire rope is wound around a pulley with one end of the wire rope fixed to the support member and the other end thereof fixed to the fixed side member.

3. The X-ray imaging apparatus as recited in claim 1, wherein the engaging member is a pin provided with a recess capable of accommodating the wire rope and configured such that a bottom surface of the recess is capable of coming into contact with the wire rope.

4. The X-ray imaging apparatus as recited in claim 2, wherein the engaging member is a pin provided with a recess capable of accommodating the wire rope and configured such that a bottom surface of the recess is capable of coming into contact with the wire rope.

5. An X-ray imaging apparatus comprising:
a support;
a support arm arranged in an ascendable and descendable manner with respect to the support and configured to support an X-ray tube and;
a pair of pulleys provided on an upper portion of the support;
a pair of wire ropes each wound around the corresponding pulley with one end of the wire rope fixed to the support arm and the other end thereof fixed to the support; and
a pair of engagement mechanisms each including an engaging member movable between an engagement position engageable with a hole formed in the support and a separation position spaced apart from the hole and a biasing means biasing the engaging member toward the engagement position, the pair of engagement mechanisms being provided on the support arm so as to correspond to the pair of wire ropes,
wherein the engaging member of the engagement mechanism is arranged at the separation position against a biasing force of the biasing means in a state in which the engaging member is in contact with the wire rope.

6. The X-ray imaging apparatus as recited in claim 5, further comprising:
a second support configured to support the support in an ascendable and descendable manner;
a pair of second pulleys provided on an upper portion of the second support;
a pair of second wire ropes each wound around the corresponding second pulley with one end of the second wire rope fixed to the support and the other end thereof fixed to the second support;
a pair of second engagement mechanisms each including a second engaging member movable between an engagement position engageable with a hole formed in the second support and a separation position spaced apart from the hole and a second biasing means biasing the second engaging member toward the engagement position, the pair of engagement mechanisms being provided on the support so as to correspond to the pair of second wire ropes,
wherein the second engaging member of the second engagement mechanism is arranged at the separation position against a biasing force of the second biasing means in a state in which the second engaging member is in contact with the second wire rope.

\* \* \* \* \*